United States Patent
Park

(10) Patent No.: US 7,043,306 B2
(45) Date of Patent: May 9, 2006

(54) THERMAL THERAPY DEVICE AND THERAPY SYSTEM USING THE SAME

(75) Inventor: Mi-Ja Park, Chungcheongnam-Do (KR)

(73) Assignee: Migun Medical Instrument Co., Ltd., Chungcheongnam-Do (KR)

( * ) Notice: Subject to any disclaimer, the term of this patent is extended or adjusted under 35 U.S.C. 154(b) by 138 days.

(21) Appl. No.: 10/606,972

(22) Filed: Jun. 27, 2003

(65) Prior Publication Data

US 2004/0082983 A1    Apr. 29, 2004

(30) Foreign Application Priority Data

Oct. 29, 2002    (KR) ................. 20-2002-0032238 U

(51) Int. Cl.
*A61F 7/12*    (2006.01)

(52) U.S. Cl. ............................ 607/99; 607/102; 601/94

(58) Field of Classification Search ............... 607/90, 607/91, 96–102, 154, 156; 606/201, 204, 606/237–245; 601/19–20, 84–99
See application file for complete search history.

(56) References Cited

U.S. PATENT DOCUMENTS 5,330,416 A * 7/1994 Masuda et al. ............... 601/52
6,454,732 B1 * 9/2002 Lee ............................ 601/101
6,591,141 B1 * 7/2003 Lee ............................. 607/98
6,606,520 B1 * 8/2003 Lee ............................. 607/98
2003/0163176 A1 * 8/2003 Bae ............................. 607/96
2004/0044384 A1 * 3/2004 Leber et al. ................. 607/88

FOREIGN PATENT DOCUMENTS

WO    WO 00/56262    * 9/2000

* cited by examiner

*Primary Examiner*—Roy D. Gibson
(74) *Attorney, Agent, or Firm*—G W i P S

(57) ABSTRACT

A heat therapy device and therapy system is provided comprising a plurality of acupressure knobs having superconductive and far-infrared emitting material attached to it. This therapy device is slightly bent up at both ends for comforting the patients. The therapy system is configured more than one therapy device comprising: upper and lower bodies, control boxes, upper control panels connected to the upper control boxes, motors installed under the upper and lower bodies, pulleys installed at the opposite the motors, upper and lower rails installed between the motors and pulleys, timing belts positioned between the upper rails and the lower rails that directly connected to the motors and pulleys; upper and lower mobile units coupled with the timing belts and seated on the upper and lower rails, each mobile unit installed with the multiple heat therapy devices, and other heat therapy devices formed the left and right sides of upper rails.

8 Claims, 12 Drawing Sheets

THERMAL THERAPY DEVICE AND THERAPY SYSTEM USING THE SAME

BACKGROUND OF THE INVENTION

1. Field of the Invention

The present invention relates to a heat therapy device and a heat therapy system for applying acupressure and thermal treatment to aching parts of a patient's body using high-temperature heat and far-infrared rays emitted from the heat therapy device, thereby preventing and healing various diseases. More specifically, the present heat therapy device is provided on the upper surface thereof with a plurality of upwardly protruding acupressure knobs, to which highly thermally conductive and far-infrared emitting material is attached, and both side portions of the device are curved upward and are provided with handles.

2. Description of the Related Art

Generally, the human body has a plurality of vital acupuncture points. These acupuncture points have been widely utilized and developed in folk remedies. Namely, where acupressure and massage treatments are applied on the acupuncture points, cells of that compressed region around the acupuncture points emit heat. At this time, waste matter is discharged therefrom, and consequently the acupuncture points are opened up, thereby achieving a state suitable for certain treatments.

Examples of well known physical therapy apparatuses using the above method generally include a heat therapy apparatus adapted to apply acupressure and thermal treatment to aching parts of the patient's body using a helium lamp, an infrared lamp and so on, and a high-frequency therapy apparatus using a high-frequency lamp.

In order to use the above therapy apparatus, the patient must first position the apparatus accurately on the acupuncture points around spinal joints, then move it to other acupuncture points around other spinal joints at regular time intervals.

Such a therapy method, however, has a problem that it is difficult for motor impaired patients to use the therapy apparatus because the patient has to position the therapy apparatus on the spinal joints by himself/herself, and also move it to the other spinal joints at regular time intervals by himself/herself.

In addition, it is difficult for most patients to accurately position the therapy apparatus on the acupuncture points around the spinal joints. Consequently, most patients cannot effectively use the therapy apparatus.

A heat therapy device of a heat therapy system, designed by recognizing the above problems, is disclosed in a utility model registration filed in the Korean Industrial Property Office as Serial No. 2000-0201798. The disclosed heat therapy system is provided with a plurality of acupressure heads integrated with far-infrared emitting material. The heat therapy system has a body provided at its bottom surface with heating elements. The heating elements are arranged at equal intervals, and, especially, are densely arranged in recessed portions under the respective acupressure members.

In addition, a utility model registration, filed in the Korean Industrial Property Office as Serial No. 2000-0170080, discloses a heat therapy device of a heat therapy system constructed in such a fashion that the middle portion of the heat therapy device is indented at both side surfaces thereof, and handles are provided in both indented side surfaces of the middle portion, thereby allowing the patient to easily hold the heat therapy device to aching parts of his/her body while gripping the handles. This configuration of the heat therapy device enables the healing of the entire body to some extent.

The conventional techniques as stated above, however, have problems in that it is impossible to effectively apply the heat therapy device of the heat therapy system to the entire body without restriction, and to simultaneously apply acupressure and thermal treatment to aching parts of the patient's body.

In short, the heat therapy system using the heat therapy device is a physical therapy apparatus for applying acupressure and thermal treatment around the spinal joints of the patient using high-temperature heat and far-infrared rays emitted from the heat therapy device, thereby preventing and healing various diseases. Namely, the heat therapy device reciprocates horizontally and vertically, thereby applying acupressure and thermal treatment around the spinal joints of the patient.

FIGS. 1 and 2 are a perspective view and a sectional view, illustrating a conventional heat therapy system. As shown in FIGS. 1 and 2, a bed-type conventional heat therapy system comprises a mattress-shaped body 1*, a motor 2*, a chain 3*, a plurality of carriers 4*, a rail 5*, a plurality of moving plates 6* mounted on the respective carriers 4*, a curved rail 7*, and plurality of heat therapy devices 10* mounted on the respective moving plates 6*. In operation, as the chain 3* is driven by the motor 2*, the carriers 4* reciprocate linearly along the rail 5*. Along with the reciprocating movement of the carriers 4*, the moving plates 6* reciprocate vertically along the curved rail 7*.

Considering the external appearance of the conventional heat therapy bed, the beat therapy bed comprises a main mattress 100*, onto which the patient's upper body is laid, and an auxiliary mattress 101*, onto which the patient's lower body is laid. By covering these mattresses with cloth and leather sheets after installing a sponge having a certain thickness on the mattresses, the heat therapy bed is completed. In use, when the patient operates the motor and heat therapy devices using a remote control while lying on the heat therapy bed, the heat therapy devices reciprocate horizontally and vertically, thereby applying acupressure and thermal treatment to the cervical vertebrae, thoracic vertebrae, lumbar vertebrae and so on of the patient.

The conventional heat therapy devices are adapted to vertically reciprocate along the spinal curvature of the patient lying on the mattresses, thereby applying acupressure to acupuncture points around the spine of the patient, and applying thermal treatment to the acupuncture points using high-temperature heat and far-infrared rays emitted from the heat therapy devices.

As seen from the above description, in order to increase the healing effect, the conventional heat therapy bed has a relatively complex structure with a plurality of carriers driven by the motor to reciprocate horizontally, and a plurality of the heat therapy devices installed on the respective carriers to apply acupressure and thermal treatment to aching parts of the patient. That is to say, in order to install a plurality of the heat therapy devices for increasing the effects of acupressure and thermal treatment, the conventional heat therapy bed is installed with a plurality of carriers. This deteriorates operability and reliability thereof, as well as increasing its manufacturing cost.

In order to solve the above problems, a utility model registration, filed in the Korean Industrial Property Office as Serial No. 2000-0288224, discloses a device for vertically reciprocating heat therapy devices. The device is configured in such a fashion that a carrier, driven by a motor to reciprocate horizontally, is equipped on both sides with brackets adapted to rotate around hinge shafts and linkages, and both brackets are provided with a pair of heat therapy devices, thereby increasing the effects of acupressure and thermal treatment to the acupuncture points. In addition, the device is constructed to ensure smooth operation of the carrier and heat therapy devices, thereby improving productivity and reducing manufacturing cost.

The device for vertically operating the heat therapy devices, however, has problems in that it cannot adjust the strength of acupressure and thermal treatment according to the different body shape and aching parts of the patient, and that the heat therapy devices coupled to the carrier provided in a lower mattress cannot move according to the motion of the patient's legs, thereby deteriorating the heat therapy effect. In addition, in case of the device's failure, the patient has to disassemble the device to repair it.

SUMMARY OF THE INVENTION

Therefore, the present invention has been created in view of the above problems, and it is an object of the present invention to provide a heat therapy device for a heat therapy system that is configured in such a fashion that it simultaneously applies acupressure and thermal treatment to aching parts of the patient's body and may be effectively used on any regions of the patient's body without restriction, thereby maximizing the healing effect of the system and allowing it to be widely used on the patient's entire body.

It is another object of the present invention to enable the patient to adjust the strength of acupressure and thermal treatment according to their own particular body shape and aching parts, thereby preventing the deterioration of the thermal treatment effect thereof due to the different body shapes of the patients.

In accordance with the present invention, the above and other objects can be accomplished by the provision of a heat therapy device comprising: a plurality of upwardly protruding acupressure knobs on its upper surface, to which is attached highly thermally conductive and far-infrared emitting material; an indented middle portion; both side portions curved upward at a constant angle to allow them to come into close contact with the patient's body, especially the back or abdomen of the patient; handles formed at respective upper ends of both side surfaces of the heat therapy device; a digital temperature display window installed on one side of an upper surface of the heat therapy device; upper and lower temperature adjustment buttons installed to one side of the temperature display window; an ON/OFF button of toggle type, provided between the upper and lower temperature adjustment buttons; and an electric power line formed on one side surface of the heat therapy device under one of the handles of the heat therapy device.

In accordance with one aspect of the present invention, the above and other objects can be accomplished by the provision of a heat therapy system using heat therapy devices, the heat therapy system comprising: upper and lower bodies; control boxes formed at adjacent portions of the upper and lower bodies and adapted to control their respective components; control panels shaped like a "⊏-shaped" plate and hinged such that each control panel is connected on one side to an upper side of its respective control box through connectors, thereby facilitating service of the control boxes; motors formed at a center position of the lower portions of the upper and lower bodies, respectively; pulleys formed on opposite sides of the motors; upper and lower rails installed between the motors and pulleys and arranged in two rows to correspond to the spine of the body; timing belts positioned along a central axis between the upper and lower rails and directly connected to the motors and pulleys, each timing belt being formed with bosses at its lower surface; upper and lower mobile units coupled with the timing belts and seated on the upper and lower rails, the upper and lower mobile units being formed with a plurality of heat therapy devices; two other heat therapy devices formed on the tipper body, the heat therapy devices being formed on left and right sides of the upper rails and adapted to apply acupressure and thermal treatment to both arms of the patient; and a portable heat therapy device installed to apply acupressure on the front part of the patient lying on his/her back on the heat therapy system for applying acupressure on the body using the heat therapy devices.

DESCRIPTION OF THE PREFERRED EMBODIMENTS

Figure 1:
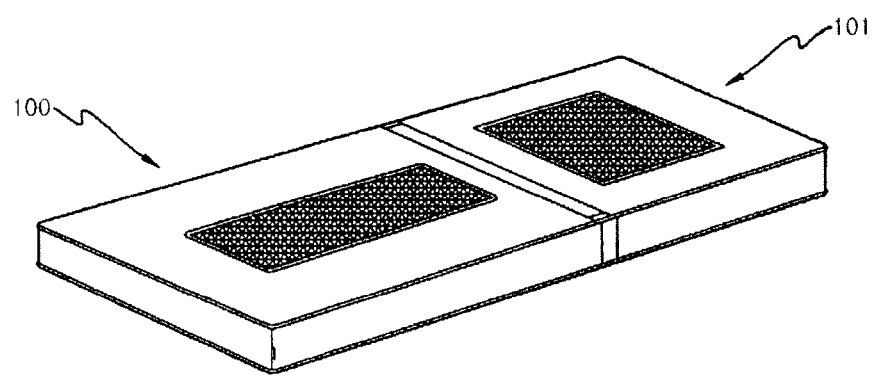
FIG. 1 is a perspective view illustrating a conventional heat therapy system.
Figure 2:
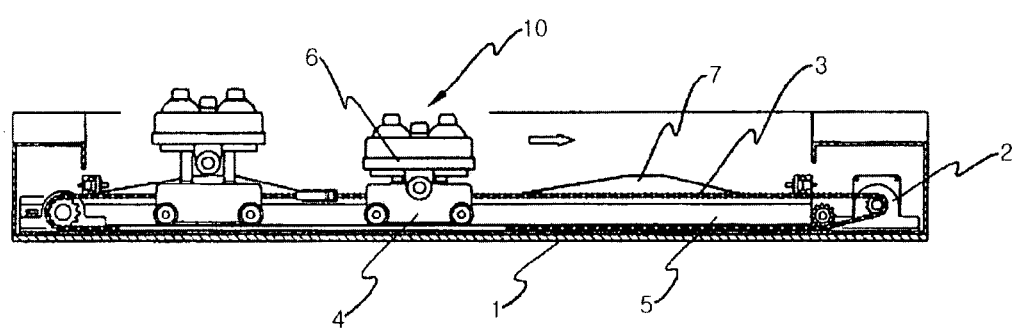
FIG. 2 is a sectional view illustrating the conventional heat therapy system as installed.
Figure 3:
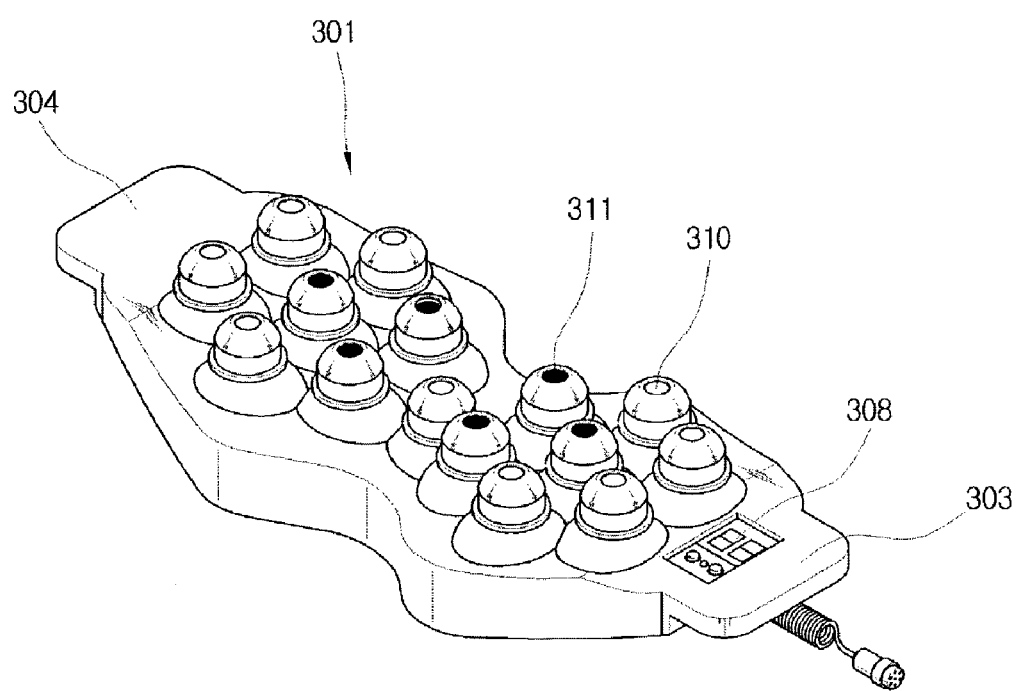
FIG. 3 is a perspective view illustrating a heat therapy device in accordance with the present invention.
Figure 4A:
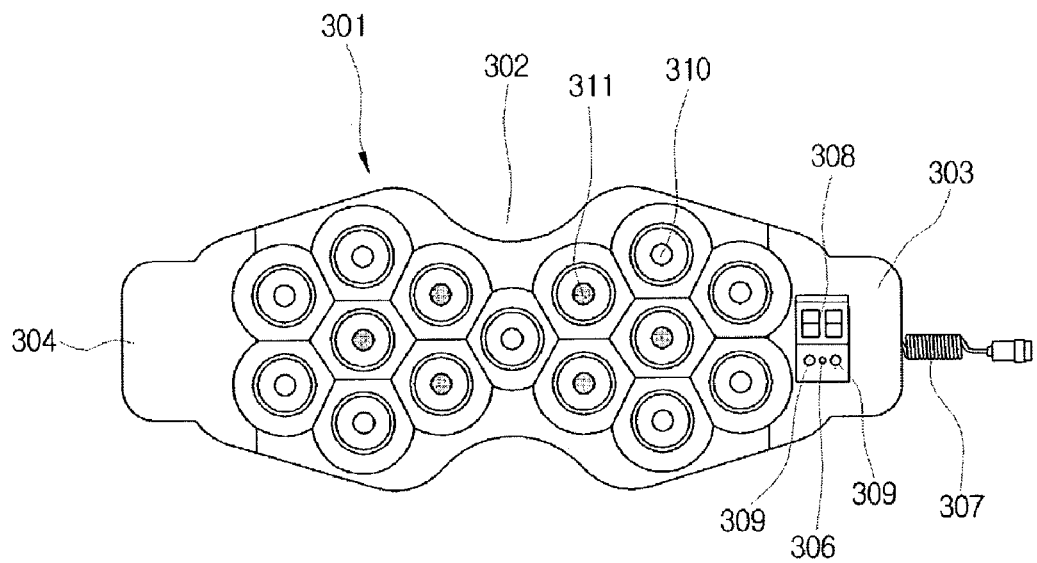
FIGS. 4a and 4b are a plan view and side view, respectively, illustrating the heat therapy device according to the present invention.
Figure 4B:
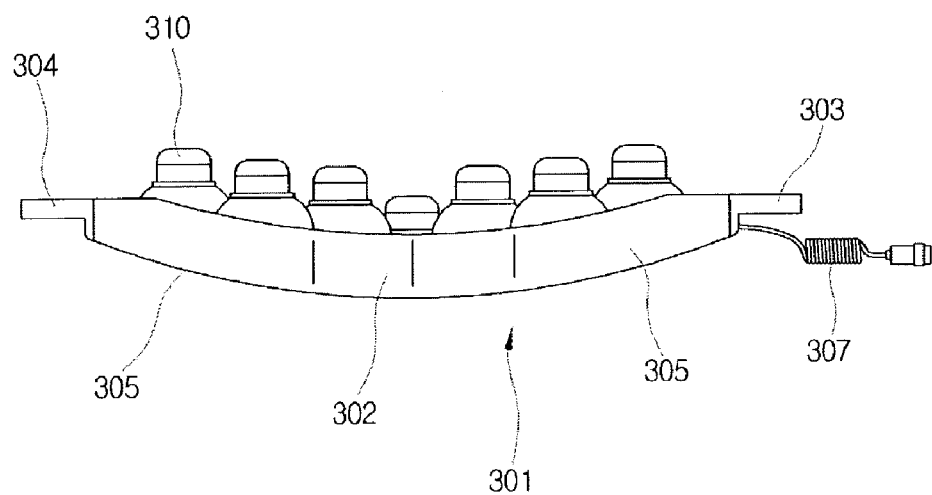
Figure 5:
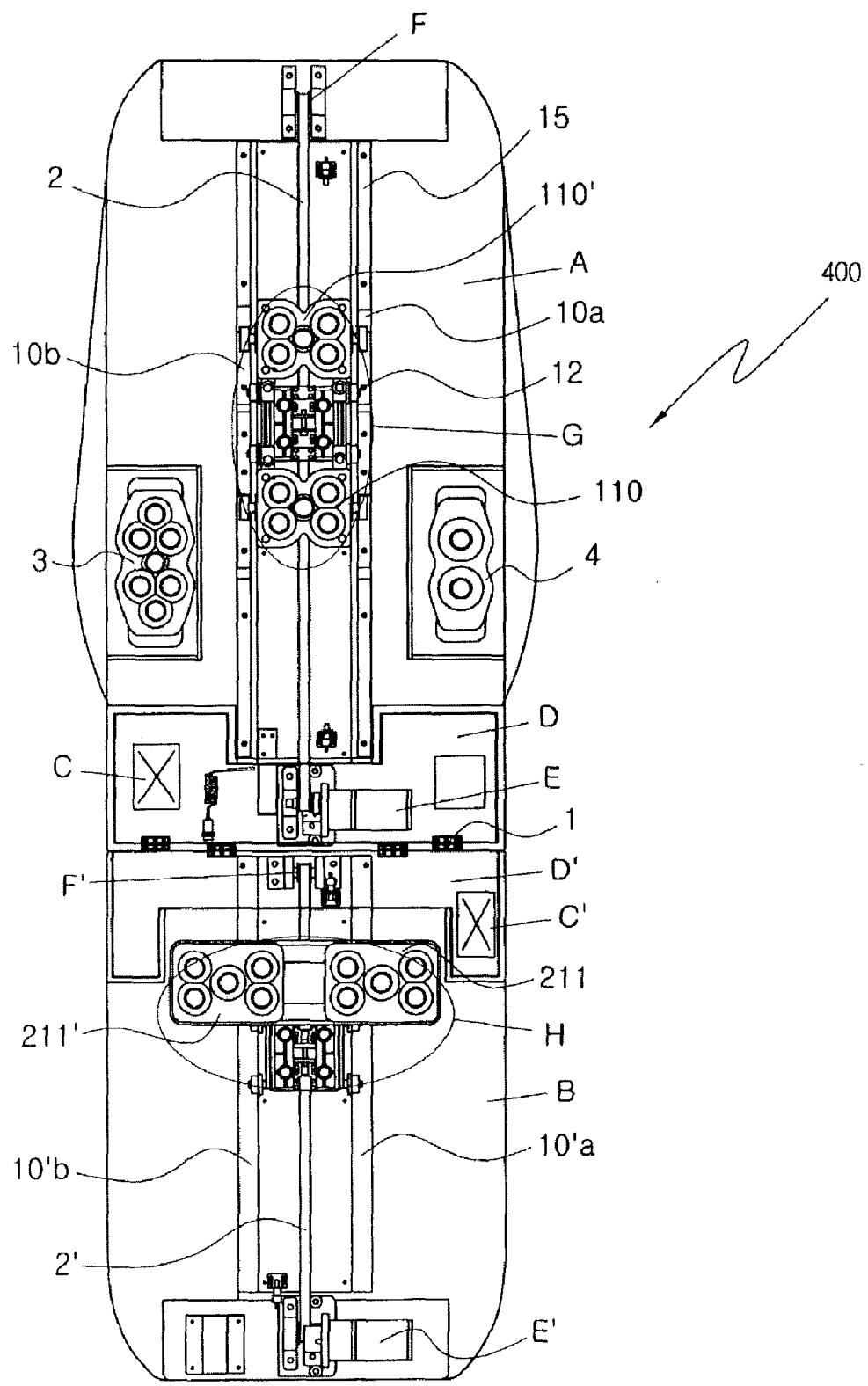
FIG. 5 is a plan view illustrating a heat therapy system in accordance with the present invention.
Figure 6:
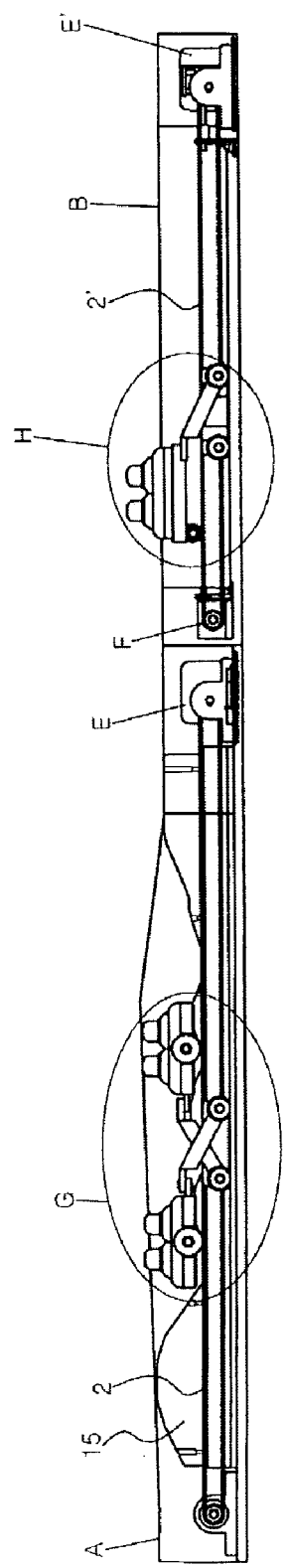
FIG. 6 is a side view illustrating the heat therapy system according to the present invention.
Figure 7:
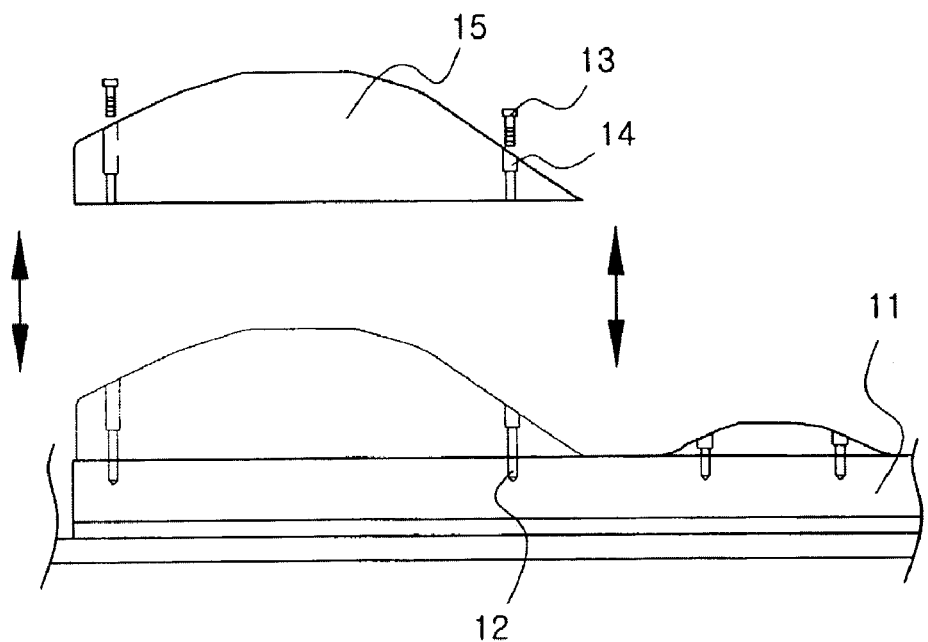
FIG. 7 is a side view illustrating upper rails in accordance with the present invention.
Figure 10:
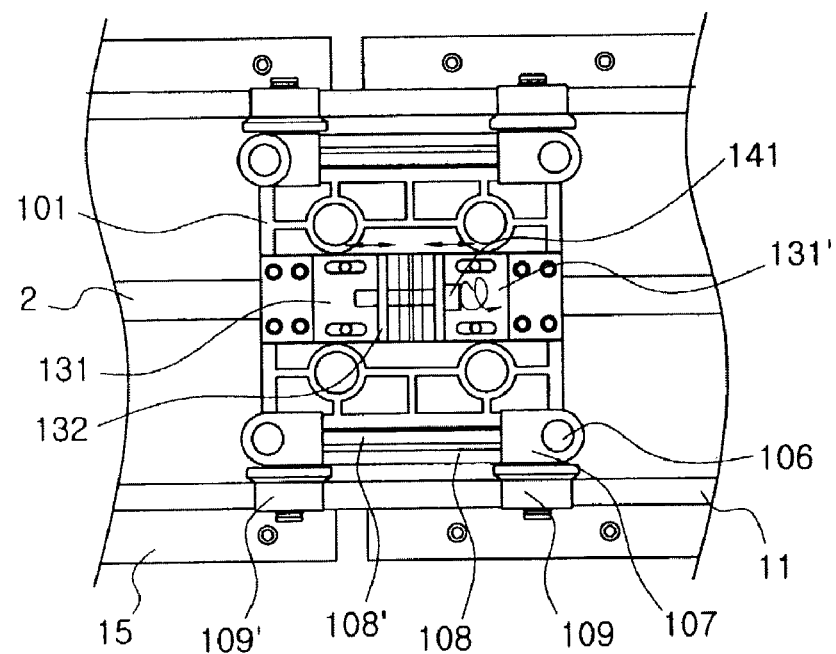
FIG. 10 is a plan view illustrating the tensile force adjustment device as installed according to the present invention.
Figure 8:
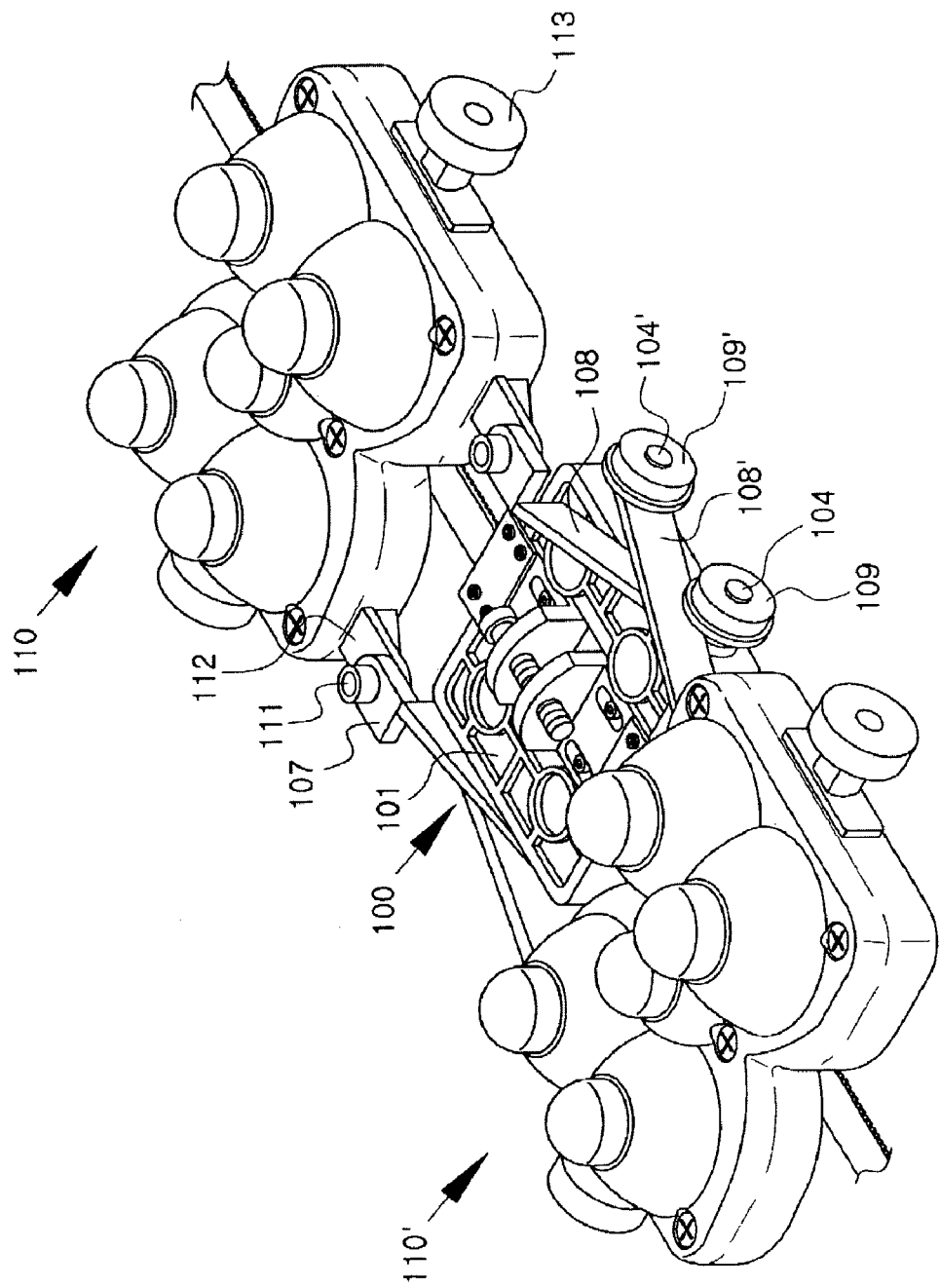
FIG. 8 is a perspective view illustrating an upper mobile unit in accordance with the present invention.
Figure 9:
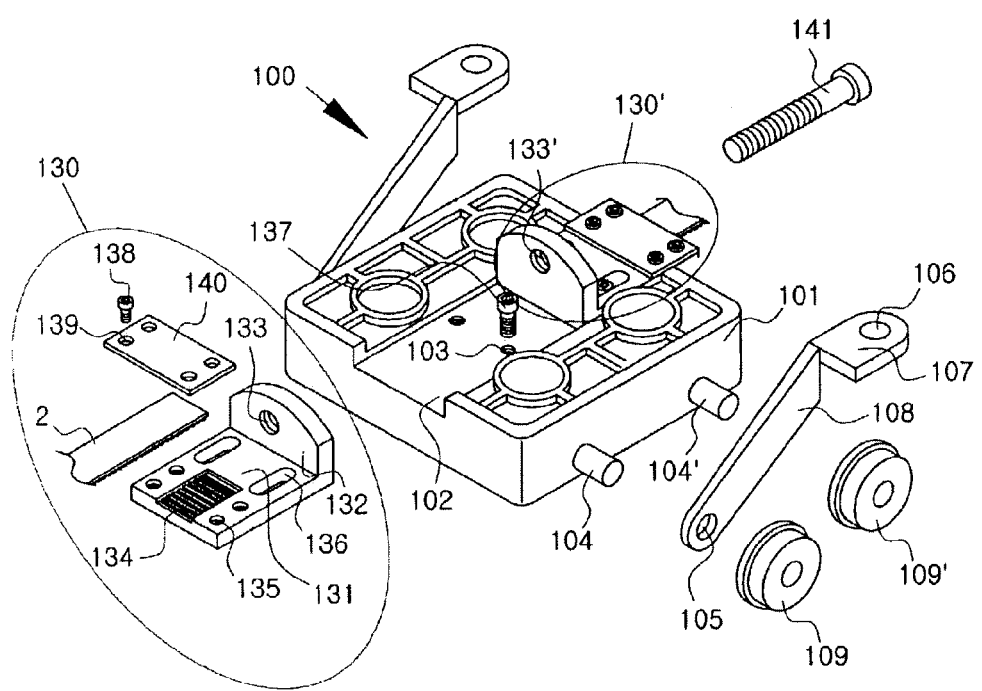
FIG. 9 is an exploded view illustrating a tensile force adjustment device in accordance with the present invention.
Figure 11:
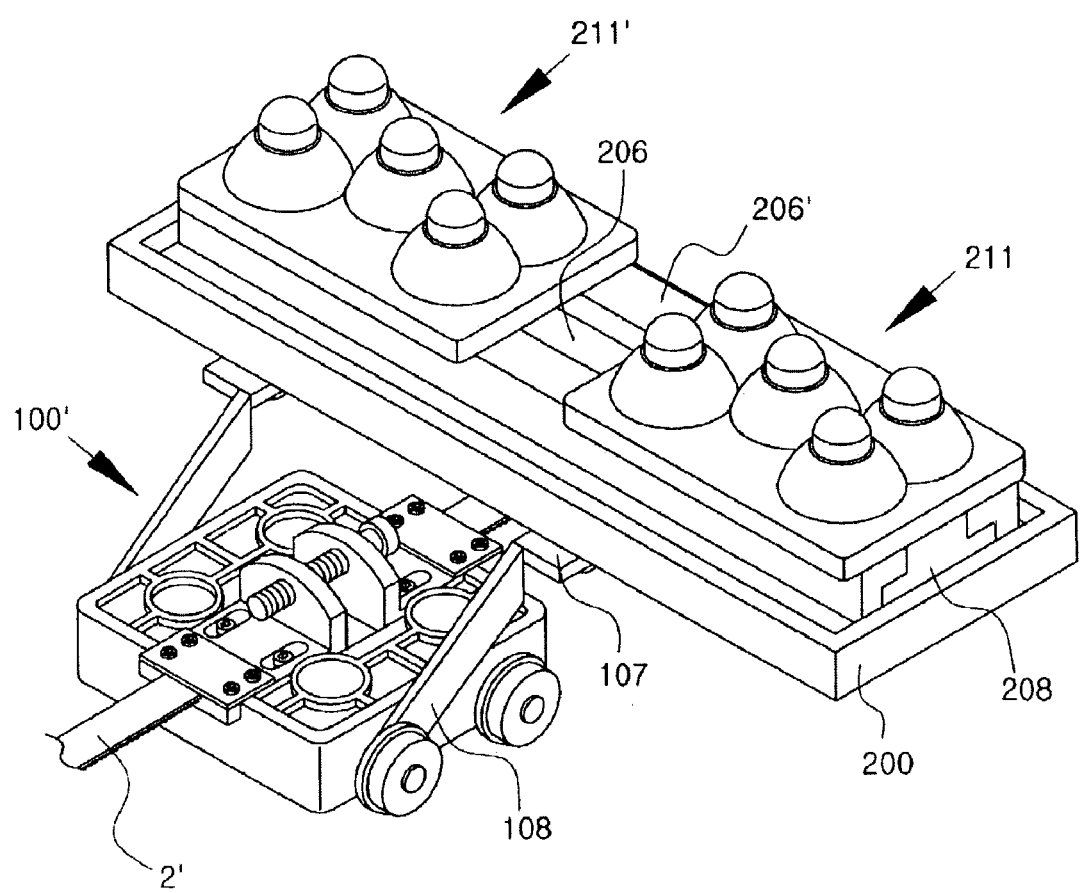
FIG. 11 is a perspective view illustrating a lower mobile unit in accordance with the present invention.
Figure 12:
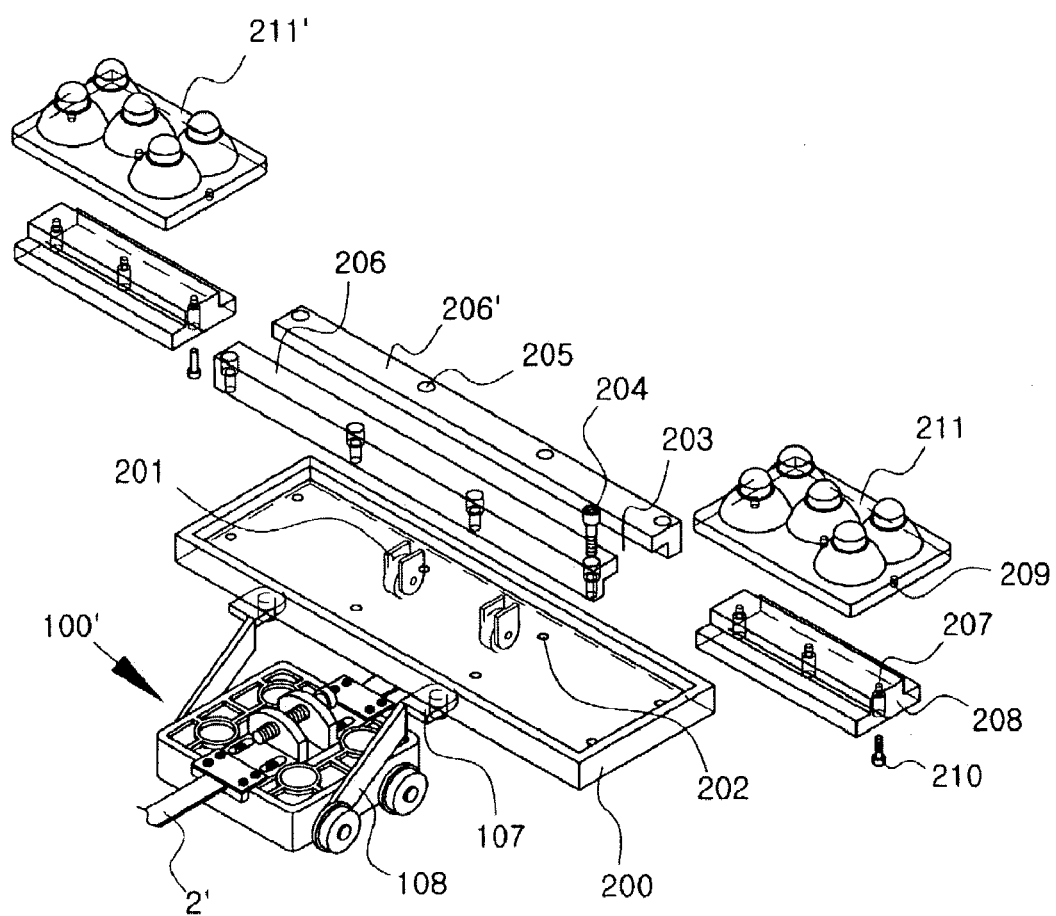
FIG. 12 an exploded view illustrates the lower mobile unit of the present invention.
Figure 13:
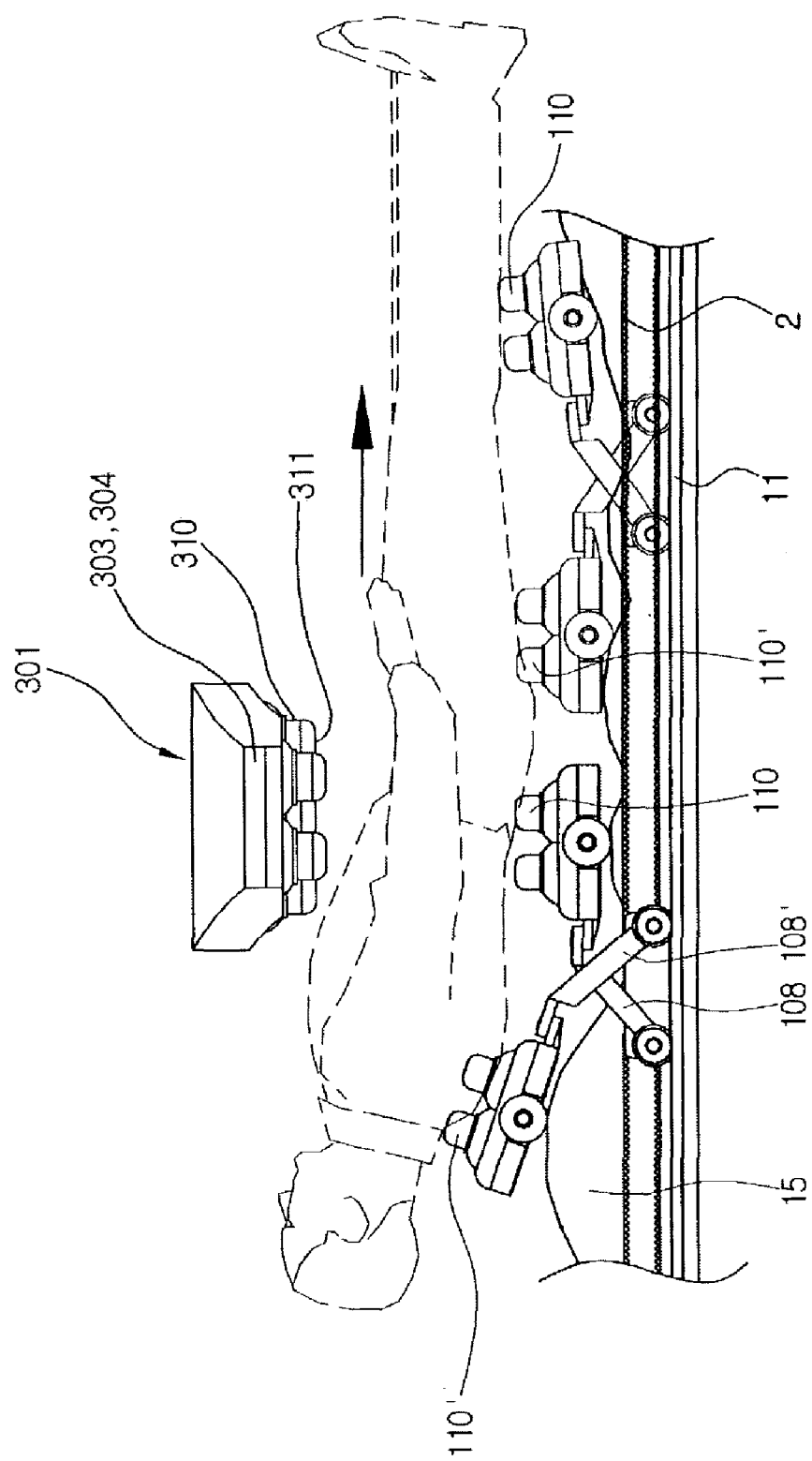
FIG. 13 is a view illustrating the operation of the upper mobile unit according to the present invention.
Figure 14A:
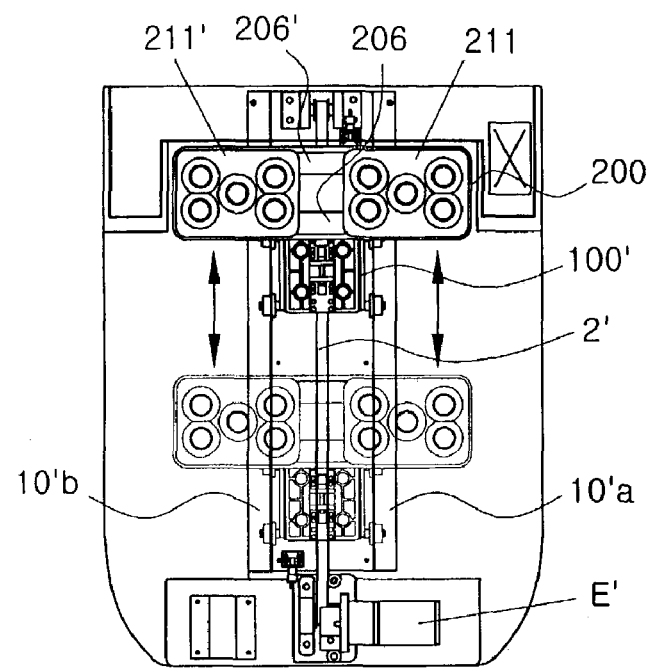
FIG. 14 is a plan view illustrating the operation of the lower mobile unit according to the present invention.
Figure 14B:
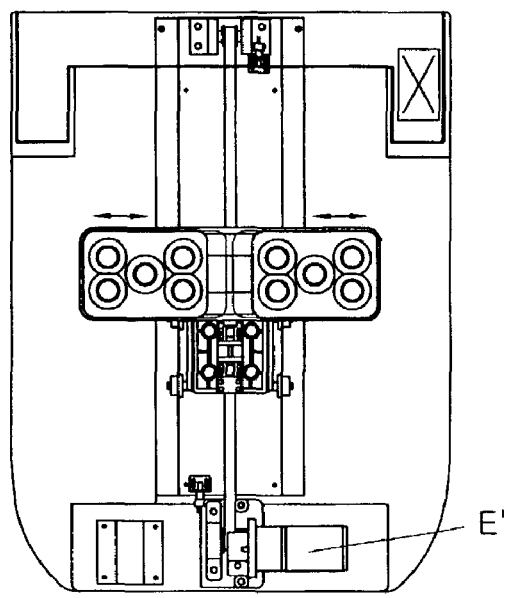

FIG. 3 is a perspective view illustrating a heat therapy device in accordance with the present invention. FIGS. 4a and 4b are a plan view and side view, respectively, illustrating the heat therapy device according to the present invention. As shown in FIGS. 3 to 4b, the heat therapy device, designated by reference numeral 301, comprises a middle portion 302, handles 303 and 304, both end portions 305, an ON/OFF button 306, an electric power line 307, a temperature display window 308, upper and lower temperature adjustment buttons 309 and 309', acupressure knobs 310, and highly thermally conductive and far-infrared emitting material 311.

Considering the structure of the heat therapy device 301 according to the present invention in detail, it is provided at its upper surface with a plurality of upwardly protruding acupressure knobs 310, and each of the acupressure knobs 310 highly thermally conductive and far-infrared emitting material 311 attached to it. The middle portion 302 of the heat therapy device 301 is indented, and both side portions 305 thereof are curved upwardly at a constant angle to allow them to come into close contact with certain regions of the patient, especially the back or abdomen.

The handles 303 and 304 are formed at the upper ends of both side surfaces of the heat therapy device 301. The digital temperature display window 308 is installed on one side of the upper surface of the heat therapy device 301, and the upper and lower temperature adjustment buttons 309 and 309' are installed to one side of the temperature display window 308.

The ON/OFF button 306, of toggle type, is provided between the upper and lower temperature adjustment buttons 309 and 309', and the electric power line 307 is drawn from one side surface of the heat therapy device 301 under one of the handles 303.

Now, the method of using the present invention constructed as stated above is described. First, the electric power line 307 is connected to a power supply, then the temperature of the heat therapy device 301 is appropriately adjusted using the temperature adjustment buttons 309 and 309'. After that, as the patient brings the heat therapy device 301 into contact with aching parts of the body while gripping the handles 303 and 304, the acupressure knobs 310 come into close contact with corresponding acupuncture points of the body, thereby applying acupressure and thermal treatment to the body.

During operation, by virtue of the highly thermally conductive and far-infrared emitting material 311 attached to the respective acupressure knobs 310, the time required for the acupressure knobs 310 to generate heat is reduced and a large amount of far-infrared rays are emitted, thereby increasing the healing effect thereof.

FIGS. 5 to 14 are views illustrating a heat therapy system in accordance with the present invention. As shown in FIGS. 5 to 14, the heat therapy system in accordance with the present invention, designated by reference numeral 400, comprises connectors 1, upper and lower timing belts 2 and 2', heat therapy devices 3, 4, 110, 110', 211 and 211', upper rails 10a and 10b, lower rails 10'a and 10'b, auxiliary rails 11, 206 and 206', screw holes 12, 14, 133 and 133', screws 13, 137, 138, 204 and 210, perforated holes 105, 106, 139 and 205, curved rail plates 15, carriers 100 and 100', a body 101, a coupling groove 102, screw bores 103, 202 and 209, hinges 104 and 104', coupling portions 107 and 112, linkages 108 and 108', rollers 109, 109', 113 and 201, a protrusion 111, a bracket 200, a T-shaped groove 203, a T-shaped insertion member 208, a first tensile force adjustor 130, a second tensile force adjustor 130', a lower tensile force adjustment plate 131, an upper tensile force adjustment plate 132, belt fastening slits 134, fixing holes 135, movement slots 136, an upper fixing plate 140, a tensile force adjustment screw 141, an upper body A, a lower body B, control boxes C and C', upper control panels D and D', motors E and E', pulleys F and F', an upper mobile unit G, a lower mobile unit H and a tensile force adjustment device I. The heat therapy system 400 is completed by adding the heat therapy device 301.

Explaining the construction of the heat therapy system 400 in detail, the heat therapy system 400 comprises the upper and lower bodies A and B defining a receiving space therein. The upper and lower bodies A and B are provided with the control boxes C and C' at adjacent portions thereof, which are adapted to control the respective components of the upper and lower bodies A and B. The respective control boxes C and C' are connected at their upper sides to the control panels D and D', which are shaped like a "⊏-shaped" plate, through the connectors 1. This configuration of the control panels D and D' facilitates service of the control boxes C and C'. The upper and lower bodies A and B are provided with the motors E and E' at the center positions of the their respective lower portions, the pulleys F and F' on opposite sides of the motors E and E', and upper and lower rails 10a, 10b, 10'a and 10'b installed between the motors E and E' and pulleys F and F', respectively. The upper and lower rails 10a, 10b, 10'a and 10'b are arranged on both sides to correspond to the patient's spine. Between the upper and lower rails 10a, 10b, 10'a and 10'b, the timing belts 2 and 2' are positioned along a central axis therebetween and are directly connected to the motors E and E' and pulleys F and F', respectively. Each timing belt 2 or 2' is formed with bosses at its lower surface. The heat therapy system 400 comprises the upper and lower mobile units G and H, which are coupled with the timing belts 2 and 2', respectively, and seated on the upper and lower rails 10a, 10b, 10'a and 10'b. The upper and lower mobile units G and H are formed with a plurality of the heat therapy devices 110, 110', 211 and 211'. In addition to the heat therapy devices 110, 110', 211 and 211', two other heat therapy devices 3 and 4 are formed on the upper body A. The heat therapy devices 3 and 4 are formed on left and right sides of the upper rails 10a and 10b and adapted to apply acupressure and thermal treatment to both arms of the patient.

Each of the upper rails 10a and 10b comprises the rail 11 formed at its upper portion with a plurality of screw holes 12, and a plurality of the detachable curved rail plates 15 formed at their upper portions with a plurality of screw holes 14. The curved rail plates 15 are arranged at regular intervals. Through the screw holes 14 of the curved rail plates 15, screws 13 are fastened to the upper portion of the rail 11.

The upper mobile unit G comprises the carrier 100 having a tensile force adjustment device I at a central portion thereof. The carrier 100 has two pairs of linkages 108 and 108' formed with the coupling portions 107 on one side. The coupling portions 107 are adapted to be coupled with the coupling portions 112 of the upper mobile unit G. Each coupling portion 112 is formed with a protrusion 111 extending upward from its upper surface. The upper mobile unit G further has the heat therapy devices 110 and 110' including a pair of rollers 113 on both side surfaces.

The upper carrier 100 comprises the square body 101 formed at a center portion of its upper surface with the linear coupling groove 102 and a pair of the screw bores 103. The tensile force adjustment device I is coupled to the upper side of the coupling groove 102 of the body 101 and adapted to adjust the tension of the timing belt 2. The body 101 includes two pairs of hinges 104 and 104' formed at both side surfaces thereof. Each of the linkages 108 and 108' includes perforated holes 105 and 106 at both end portions, and at one end the coupling portion 107 is formed. One of the perforated holes 106 is formed at the coupling portion 107, and the other perforated hole 105 is used for insertion of the hinge 104 or 104'. The respective linkages 108 and 108' are formed with the rollers 109 and 109' at opposite outer sides thereof. The rollers 109 and 109' are adapted to be coupled around the hinges 104 and 104', respectively.

The tensile force adjustment device I comprises the first tensile force adjustor 130 formed at one side of the body 101, and the second tensile force adjustor 130' formed at the other side of the body 101. The second tensile force adjustor 130' has the same structure as that of the first tensile force adjustor 130. In addition, the tensile force adjustment device I comprises the tensile force adjustment screw 141 fastened into the screw holes 133 and 133' that are formed at the first and second tensile force adjustors 130 and 130' and adapted to adjust the tension of the timing belt 2.

The first tensile force adjustor 130 is provided with the lower tensile force adjustment plate 131, and the upper tensile force adjustment plate 132. The lower tensile force adjustment plate 131 is coupled to one side of the upper center portion of the square body 101. The upper tensile force adjustment plate 132 extends upwards from one edge of the lower tensile force adjustment plate 131 and includes the tensile force adjustment screw hole 133. The lower tensile force adjustment plate 131 is formed at one side of the upper center portion thereof with the belt fastening slits 134, which are adapted to fasten one of the timing belts 2. A plurality of fixing holes 135 are formed at both sides of the belt fastening slits 134, and the movement slots 136 are formed adjacent to the fixing holes 135. The movement slots 136, especially, are arranged to correspond with a pair of the screw bores 103 formed at the body 101, thereby allowing the screw 137 to be fastened therethrough. The first tensile force adjustor 130 is also provided with the upper fixing plate 140 for preventing the withdrawal of the timing belt 2. The upper fixing plate 140 is formed with a plurality of perforated holes 139 for allowing the screws 138 to be fastened to the fixing holes 135 therethrough.

By tightening or loosening the tensile force adjustment screw 141, coupled into the screw holes 133 and 133' formed at the first and second tensile force adjustors 130 and 130', the respective lower tensile force adjustment plates 131 and 131' of the first and second tensile force adjustors 130 and 130' are moved to the left or the right, thereby adjusting the tension of the timing belt 2.

Meanwhile, the lower mobile unit H comprises the carrier 100' having the same structure as that of the carrier 100 of the upper mobile unit G, and a rectangular bracket 200 having upwardly protruding portions of a certain length. The upwardly protruding portions are coupled with the coupling portions 107 formed at the linkages 108 of the carrier 100'. The bracket 200 includes a pair of rollers 201 at the lower surface thereof, and at both sides of the upper surface thereof a plurality of screw bores 202 are linearly arranged. The rails 206 and 206', having a "⌐-shaped" cross section, are coupled to the upper side of the screw bores 202 to form a T-shaped groove 203. Each rail 206 or 206' is formed with perforated holes 205 for allowing screws 204 to be fastened to the screw bores 202 therethrough. The T-shaped insertion member 208 is fitted into the T-shaped groove 203 define between the rails 206 and 206'. The T-shaped insertion member 208 is formed with a plurality of the bores 207 linearly arranged along a central axis thereof. The lower mobile unit H is further provided with the heat therapy devices 211 and 211' disposed above the T-shaped groove 203. The heat therapy devices 211 and 211' are formed with a plurality of the screw bores 209 corresponding to the bores 207, thereby allowing the screws 210 to be fastened therethrough.

According to the construction of the heat therapy system 400 as stated above, one mobile unit, configured to reciprocate horizontally by the driving of the motor, is installed with a plurality of the heat therapy devices. The carrier 100, coupled with the timing belt 2, reciprocates linearly along the upper rail 11 by the driving of the motor E, and the heat therapy devices 110 and 110', rotatably coupled to the linkages 108 and 108' of the carrier 100, move in a vertical direction as they pass over the curved rail plates 15. That is to say, the heat therapy devices 110 and 100', coupled to the carrier 100, reciprocate horizontally, thereby applying acupressure and thermal treatment to the acupuncture points around the spine of the patient.

In addition, the operation of the lower mobile unit H formed at the lower body B is described. In the same manner as the carrier 100 of the upper body A, the carrier 100', coupled with the timing belt 2', reciprocates linearly along the lower rails 10'a and 10'b by the driving of the motor E', and the heat therapy devices 211 and 211', coupled to the rails 206 and 206', move to the left and right according to the leftward and rightward movements of the lower body of the patient. As stated above, the rails 206 and 206' define the T-shaped groove 203 therebetween, and the T-shaped groove 203 is formed above the bracket 200, which is rotatably coupled to the linkages 108 of the carrier 100'.

In operation, the heat therapy devices 211 and 211' move to the left and right according to the lower body of the patient while reciprocating horizontally due to the motor E', thereby effectively applying acupressure and thermal treatment to the lower body of the patient.

Each of the heat therapy devices 110 and 110' installed on the upper mobile unit G and the heat therapy devices 211 and 211' installed on the lower mobile units H is provided at its upper surface with a plurality of upwardly protruding acupressure knobs 310, to which is attached the highly thermally conductive and far-infrared emitting material 311. In addition, the respective heat therapy devices 110, 110', 211 and 211' are curved upward at a constant angle to allow them to come into close contact with the body, especially the back or abdomen of the patient. This maximizes the far-infrared emission effect and enables the heat therapy devices to more closely contact the patient's body, thereby improving the healing effect thereof.

Each of the heat therapy devices 3 and 4 installed at the right and left sides of the upper rails 10a and 10b is provided at its upper surface with a plurality of upwardly protruding acupressure knobs 310, to which is attached the highly thermally conductive and far-infrared emitting material 311. In addition, the heat therapy devices 3 and 4 are curved upwardly at a constant angle to allow them to come into close contact with the body, especially the back or abdomen of the patient. This maximizes the far-infrared emission effect and enables the heat therapy devices to more closely contact the patient's body, thereby improving the healing effect thereof.

As apparent from the above description, since the multiple curved rail plates 15 are adapted to be selectively attached to or detached from the upper surfaces of the upper rails 10a and 10b, it is possible to adjust the strength of acupressure and thermal treatment according to the particular shape and aching parts of any patient's body. As stated above, the upper mobile unit G is adapted to move in a vertical direction according to the curved rail plates 15 and reciprocate linearly along the rail 11 due to the motor E, and the heat therapy devices 110 and 110' are coupled to the upper mobile unit G. According to the present invention, the beat therapy devices 110 and 110' are constructed to achieve a maximum height with a minimum volume. This prevents the thermal treatment effect of the devices from deteriorating due to the different body shapes of patients, as well as ensuring the smooth operation thereof. Further, according to the present invention, the lower mobile unit H, adapted to reciprocate linearly along the lower rails 10'a and 10'b due to the motor E' includes with a pair of the heat therapy devices 211 and 211' at its upper surface, which are adapted to move to the left and right according to the movements of the patient. This prevents the deterioration of the thermal treatment effect of the devices due to the movements of the lower body. Furthermore, by virtue of the "⊏-shaped" upper control panels D and D', provided on the upper side of the control boxes C and C' and articulated, the control boxes C and C' can be easily repaired without disassembling the upper and lower bodies A and B.

The heat therapy device of the present invention can apply acupressure and thermal treatment to aching parts of the patient. Further, by virtue of the highly thermally conductive and far-infrared emitting material 311 attached to the respective acupressure knobs 310, it is possible to reduce the time required for the acupressure knobs to generate heat and to emit a large amount of far-infrared rays, thereby enhancing the healing effect thereof.

The heat therapy device 301 is configured so that both end portions thereof are curved upward at a certain angle, thereby enabling it to be widely applied on the entire body of the patient, unlike any conventional heat therapy systems.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A heat therapy device comprising:
    a plurality of upwardly protruding acupressure knobs on its upper surface, each of the acupressure knobs having highly thermally conductive and far-infrared emitting material attached to it,
    an indented middle portion with two sides portions,
    both side portions curved upwardly at a constant angle to allow the knobs to come into close contact with the patient's body, especially the back or abdomen of the patient,
    handles formed at respective upper ends of both side portions of the heat therapy device,
    a digital temperature display window installed at one side of an upper surface of the heat therapy device,
    upper and lower temperature adjustment buttons installed to one side of the temperature display window,
    an on/off button, of toggle type, provided between the upper and lower temperature adjustment buttons, and
    an electric power line formed at one side surface of the heat therapy device under one of the handles of the heat therapy device.

2. A heat therapy system utilizing at least one heat therapy device, the heat therapy system comprising:
    upper and lower bodies defining a receiving space therein,
    control boxes formed at adjacent portions of the upper and lower bodies and adapted to control their respective components,
    control panels shaped like a "⊏-shaped" plate and hinged such that each control panel is connected at its one side to an upper side of the respective control box through connectors, thereby facilitating service of the control boxes, the control panels being connected with electric power lines to the heat therapy devices,
    motors formed at a center position of the respective lower portions of the upper and lower bodies,
    pulleys formed at opposite sides of the motors,
    upper and lower rails installed between the motors and pulleys, respectively, the upper and lower rails being arranged in two rows to correspond to the spine of the body,
    timing belts positioned along a central axis between the upper and lower rails that are directly connected to the motors and pulleys, each timing belt being formed with bosses at its lower surface,
    upper and lower mobile units coupled with the timing belts, and seated on the upper and lower rails, the upper and lower mobile units including a plurality of heat therapy devices, and
    two other heat therapy devices formed on the upper body, the heat therapy devices being formed at left and right sides of the upper rails and adapted to apply acupressure and thermal treatment to both arms of the patient.

3. The heat therapy system as set forth in claim 2, wherein each of the upper rails comprises a rail formed at its upper portion with a plurality of screw holes, and a plurality of detachable curved rail plates arranged at regular distances and formed at their upper portions with a plurality of screw holes, whereby screws are fastened to the upper portion of the rail through the screw holes of the rail plates.

4. The heat therapy system as set forth in claim 2, wherein the upper mobile unit comprises:
    a carrier having a tensile force adjustment device at a central portion thereof,
    coupling portions adapted to be coupled with corresponding coupling portions formed at one side of each of two pairs of linkages provided in the carrier, respectively, each coupling portion being formed with an upwardly extended protrusion at its upper surface, and
    the heat therapy devices formed with a pair of rollers at both side surfaces,
    said carrier further comprising:
    a square body formed at a center portion of its upper surface with a linear coupling groove and a pair of screw bores,
    a tensile force adjustment device coupled to the coupling groove of the body and adapted to adjust the tension of one of the timing belts,
    two pairs of hinges formed at both side surfaces of the body,
    linkages, each linkage being formed at both end portions with two perforated holes and at one end with the coupling portion, one of the perforated holes being formed at the coupling portion, the other perforated hole being used for insertion of the hinge, and
    rollers formed at opposite outer sides of the respective linkages and adapted to be coupled around the respective hinges.

5. The heat therapy system as set forth in claim 4, wherein the tensile force adjustment device comprises:
    a first tensile force adjustor formed at one side of the body,
    a second tensile force adjustor formed at the other side of the body, the second tensile force adjustor having the same structure as that of the first tensile force adjustor, and
    a tensile force adjustment screw fastened into the screw holes formed at the first and second tensile force adjustors and adapted to adjust the tension of the timing belt,
    said first tensile force adjustor further comprising:
    a lower tensile force adjustment plate coupled to one side of the upper center portion of the square body,
    an upper tensile force adjustment plate extending upwards from one edge of the lower tensile force adjustment plate and formed with the tensile force adjustment screw hole, belt fastening slits formed at one side of the upper center portion of the lower tensile force adjustment plate and adapted to fasten one of the timing belts, a plurality of fixing holes formed at both sides of the belt fastening slits, movement slots adjacent to the fixing holes, the movement slots being positioned to correspond with a pair of the screw bores formed at the body, thereby allowing screws to be fastened therethrough, and an upper fixing plate for preventing the withdrawal of the timing belt, the upper fixing plate being formed with a plurality of perforated holes to allow screws to be fastened to the fixing holes therethrough.

6. The heat therapy system as set forth in claim 2, wherein the lower mobile unit comprises:

a carrier having the same structure as that of the carrier of the upper mobile unit, a rectangular bracket having upwardly protruding portions of a certain length, the upwardly protruding portions being coupled with the coupling portions formed on the respective linkages of the carrier provided in the upper mobile unit;

a pair of rollers formed at a lower surface of the bracket, a plurality of screw bores arranged linearly at both sides of an upper surface of the bracket, rails having a "⌐-shaped" cross section, the rails being coupled to an upper side of the screw bores to form a T-shaped groove, each rail being formed with perforated holes to allow screws to be fastened to the screw bores therethrough, a T-shaped insertion member adapted to be fitted into the T-shaped groove defined between the rails, the T-shaped insertion member being formed with a plurality of bores linearly arranged along a central axis thereof, and heat therapy devices disposed above the T-shaped groove and formed with a plurality of screw bores corresponding to the bores, thereby allowing screws to be fastened therethrough.

7. The heat therapy system as set forth in claim 2, wherein each of the heat therapy devices installed on the upper and lower mobile units is provided at its upper surface with a plurality of upwardly protruding acupressure knobs, which have the highly thermally conductive and far-infrared emitting material attached to them, wherein the respective heat therapy devices are curved upwards at a constant angle to allow them to come into close contact with the patient's body, especially the back or abdomen of the patient.

8. The heat therapy system as set forth in claim 2, wherein each of the heat therapy devices installed at left and right sides of the upper rails is provided at its upper surface with a plurality of upwardly protruding acupressure knobs, which have the highly thermally conductive and far-infrared emitting material attached to them, wherein the respective heat therapy devices are curved upwards at a constant angle to allow them to come into close contact with the patient's body, especially the back or abdomen of the patient.

* * * * *